United States Patent
Liang et al.

(10) Patent No.: US 11,419,761 B2
(45) Date of Patent: Aug. 23, 2022

(54) GLAUCOMA AQUEOUS HUMOR DRAINAGE DEVICE AND GLAUCOMA AQUEOUS HUMOR DRAINAGE METHOD

(71) Applicant: THE EYE HOSPITAL OF WENZHOU MEDICAL UNIVERSITY, Wenzhou (CN)

(72) Inventors: Yuanbo Liang, Wenzhou (CN); Chengtan Liu, Wenzhou (CN); Liang Wen, Wenzhou (CN); Yanqian Xie, Wenzhou (CN)

(73) Assignee: THE EYE HOSPITAL OF WENZHOU MEDICAL UNIVERSITY, Wenzhou (CN)

( * ) Notice: Subject to any disclaimer, the term of this patent is extended or adjusted under 35 U.S.C. 154(b) by 48 days.

(21) Appl. No.: 16/936,053

(22) Filed: Jul. 22, 2020

(65) Prior Publication Data
US 2022/0023097 A1   Jan. 27, 2022

(51) Int. Cl.
*A61F 9/007*   (2006.01)
(52) U.S. Cl.
CPC .................. *A61F 9/00781* (2013.01)
(58) Field of Classification Search
CPC ................... A61F 9/007; A61F 9/00781; A61F 2009/00891; A61F 2/1662; A61F 27/002
See application file for complete search history.

(56) References Cited

U.S. PATENT DOCUMENTS

| | | | | |
|---|---|---|---|---|
| 6,077,299 | A * | 6/2000 | Adelberg | A61F 9/00781 604/9 |
| 6,589,203 | B1 * | 7/2003 | Mitrev | A61F 9/00781 604/27 |
| 7,776,002 | B2 * | 8/2010 | Molteno | A61F 9/00781 604/8 |
| 7,806,847 | B2 * | 10/2010 | Wilcox | A61F 9/0017 604/8 |
| 8,287,482 | B2 * | 10/2012 | Badawi | A61F 9/00781 604/8 |
| 9,492,320 | B2 * | 11/2016 | Lynch | A61F 9/00781 |
| 10,029,009 | B1 * | 7/2018 | Berdahl | A61M 27/006 |
| 10,524,958 | B2 * | 1/2020 | Camras | A61F 9/00781 |
| 10,548,769 | B2 * | 2/2020 | Venkatraman | A61F 9/00781 |

(Continued)

OTHER PUBLICATIONS

"Daniel B. Moore, MD, Glaucoma Drainage Devices, May 6, 2021, American Academy of Ophthalmology" (Year: 2021).*

*Primary Examiner* — Susan S Su
*Assistant Examiner* — Eric Rassavong
(74) *Attorney, Agent, or Firm* — Christensen, Fonder, Dardi & Herbert PLLC

(57) ABSTRACT

A glaucoma aqueous humor drainage device and a glaucoma aqueous humor drainage method, wherein the opening and closing of a pressure valve is controlled by the change in the pressure in a cavity of the valve. When the pressure in the intraocular pressure exceeds 12 mmHg, the valve is opened, and a drainage tube connected behind the valve drains the aqueous humor to the ocular surface, reducing the patient's discomfort and dry eyes, effectively draining the aqueous humor and avoiding scarring caused by embedding the device via a conjunctival flap and operation failure caused by increase of intraocular pressure caused by generation of filtering blebs.

15 Claims, 2 Drawing Sheets

(56) References Cited

U.S. PATENT DOCUMENTS

| | | | | |
|---|---|---|---|---|
| 2002/0087111 A1* | 7/2002 | Ethier | ............... | A61F 9/00781 |
| | | | | 604/9 |
| 2004/0162545 A1* | 8/2004 | Brown | ............... | A61F 9/00781 |
| | | | | 604/541 |
| 2010/0114006 A1* | 5/2010 | Baerveldt | ........... | A61M 27/002 |
| | | | | 604/8 |
| 2012/0184892 A1* | 7/2012 | Bigler | ................ | F04B 43/14 |
| | | | | 604/9 |
| 2015/0057596 A1* | 2/2015 | Lind | ................ | A61F 9/00781 |
| | | | | 604/9 |
| 2016/0067092 A1* | 3/2016 | Lind | ................ | A61B 3/10 |
| | | | | 604/8 |
| 2016/0374856 A1* | 12/2016 | Pinchuk | ............. | A61F 9/00781 |
| | | | | 604/8 |
| 2018/0263819 A1* | 9/2018 | Roeber | ............... | A61L 31/048 |

* cited by examiner

GLAUCOMA AQUEOUS HUMOR DRAINAGE DEVICE AND GLAUCOMA AQUEOUS HUMOR DRAINAGE METHOD

FIELD OF THE INVENTION

The present invention particularly relates to the technical field of ophthalmology, and in particular to a glaucoma aqueous humor drainage device and a glaucoma aqueous humor drainage method.

BACKGROUND OF THE INVENTION

Glaucoma, as the second leading cause of blindness in the world, is a group of diseases of the optic neuropathy characterized by changes in the structure of the papilla nervi optici, resulting in defects in the visual field, ultimately leading to blindness. By 2020, approximately 79.6 million people worldwide will have glaucoma, and more than 11 million people will have glaucoma in both eyes. Lowering intraocular pressure is the only method that has proven to be scientifically effective in delaying the progression of glaucoma. Decreasing intraocular pressure in glaucoma patients can be achieved through drug, laser, and surgical treatments. Anti-glaucoma surgery currently widely used clinically includes trabeculectomy, cataract surgery alone, glaucoma-cataract combined surgery and cyclophotocoagulation. Trabeculectomy is a conventional and classical surgery for glaucoma with inevitable complications, e.g., ocular hypotension in early, shallow anterior chamber 20-40%, choroidal detachment 2%, and cystoid macular edema 1%. Surgical failure may occur in the late stage, and the problem of scarring of the filtering bleb increases with time, up to 50% in about 5 years. The complications of the filtering bleb include filtering bleb leakage, infection, ptosis, and the effects of filtering blebs on ocular surface structure and function. Refractory glaucoma in glaucoma includes glaucoma secondary to iridocorneal endothelial syndrome, glaucoma secondary to trauma, glaucoma secondary to inflammation, and failure of previous filtering surgery. This type of glaucoma is characterized by difficulty in controlling intraocular pressure using conventional means, and after conventional trabeculectomy, surgical failure due to the easier scarring of the filtering bleb. In recent years, glaucoma aqueous humor drainage valve surgery has gradually become popular. Compared with traditional trabeculectomy, this surgical method has a significantly higher success rate in the treatment of refractory glaucoma. The drainage disc is embedded under the conjunctiva by manufacturing the conjunctival flap, it is also easy to cause fibrous tissue proliferation around the drainage disc, followed by scarring around the drainage disc and the formation of encapsulated blebs that prevent the aqueous humor from spreading, resulting in the intraocular pressure rising again, causing surgery failure.

SUMMARY OF THE INVENTION

In order to solve the technical defects in the prior art, the present invention provides a glaucoma aqueous humor drainage device and a glaucoma aqueous humor drainage method, which can effectively drain aqueous humor and avoid scarring caused by embedding the device via the conjunctival flap and operation failure caused by increase of intraocular pressure caused by generation of filtering blebs.

The technical solution adopted by the present invention is as follows: a glaucoma aqueous humor drainage device comprising a device body, wherein the device body comprises a pressure valve, the pressure valve is connected with an internal drainage catheter for draining anterior chamber aqueous humor into a cavity within the pressure valve and an external drainage catheter for draining the anterior chamber aqueous humor in the cavity of the pressure valve to the ocular surface upon the pressure valve reaching a threshold value.

In an embodiment, the pressure threshold of the pressure valve is 12 mm Hg.

The two ends of the external drainage catheter are respectively connected to the cavity in the pressure valve to form an annular closed structure.

The wall of the external drainage catheter is provided with several through holes, and the anterior chamber aqueous humor is drained to the ocular surface through the through holes in the wall of the external drainage catheter.

The inner tube wall of the external drainage catheter is also covered with a semi-permeable membrane material.

The through holes are sequentially distributed at 3, 6, 9 and 12 o'clock positions of the annular closed structure formed by the external drainage catheter in a clock hands mode.

In an embodiment, the through hole is a circular pore channel with a pore diameter of 500 μm.

In an embodiment, the inner diameter of the internal drainage catheter is 1 mm, and the length of the internal drainage catheter is 8 mm.

In an embodiment, the diameter of the annular closed structure formed by the external drainage catheter is smaller than 30 mm.

The internal drainage catheter and the external drainage catheter are made of biocompatible materials.

The wall of the external drainage catheter is made of a semipermeable membrane material.

The semi-permeable membrane material has an ultrafiltration molecular weight of 500-500000 D and a pore size of 1 nm-1 μm.

One or more lead wires for fixing the external drainage catheter through tension is further arranged on the external drainage catheter.

A glaucoma aqueous humor drainage method comprises the following steps: moving an internal drainage catheter of a drainage device submerged under the superficial scleral flap 3-4 mm away from the corneal limbus, after reaching the corneal limbus, turning the internal drainage catheter into an included angle of 5°-10° with the iris to penetrate into the anterior chamber, after the internal drainage catheter is penetrated into the anterior chamber, fixing the internal drainage catheter on the surface of the superficial sclera by an absorbable line, placing a pressure valve along the radian of the sclera, opening the eyelid, and placing an external drainage catheter along the radian of the sclera and fixing under the fornix conjunctiva.

The external drainage catheter is positioned between the fornix conjunctiva and the corneal limbus, and the distances away from the upper and lower parts of the fornix conjunctiva and the corneal limbus are all 8-10 mm.

The present invention has the beneficial effects that: the present invention provides a glaucoma aqueous humor drainage device and a glaucoma aqueous humor drainage method. The opening and closing of the valve is controlled by the change in the pressure in the cavity of the pressure valve. When the pressure in the intraocular pressure exceeds 10 mmHg, the valve is opened, and a drainage tube connected behind the valve drains the aqueous humor to the ocular surface, reducing the patient's discomfort and dry eyes, effectively draining the aqueous humor and avoiding scarring caused by embedding the device via the conjunctival flap and operation failure caused by increase of intraocular pressure caused by generation of filtering blebs.

Wherein, 1—pressure valve, 2—internal drainage catheter, 3—external drainage catheter, 4—through hole, and 5—cavity, 6—left end, 7—cavity right end, and 8 lead wires.

DETAILED DESCRIPTION OF THE INVENTION

Figures 1A, 1B:
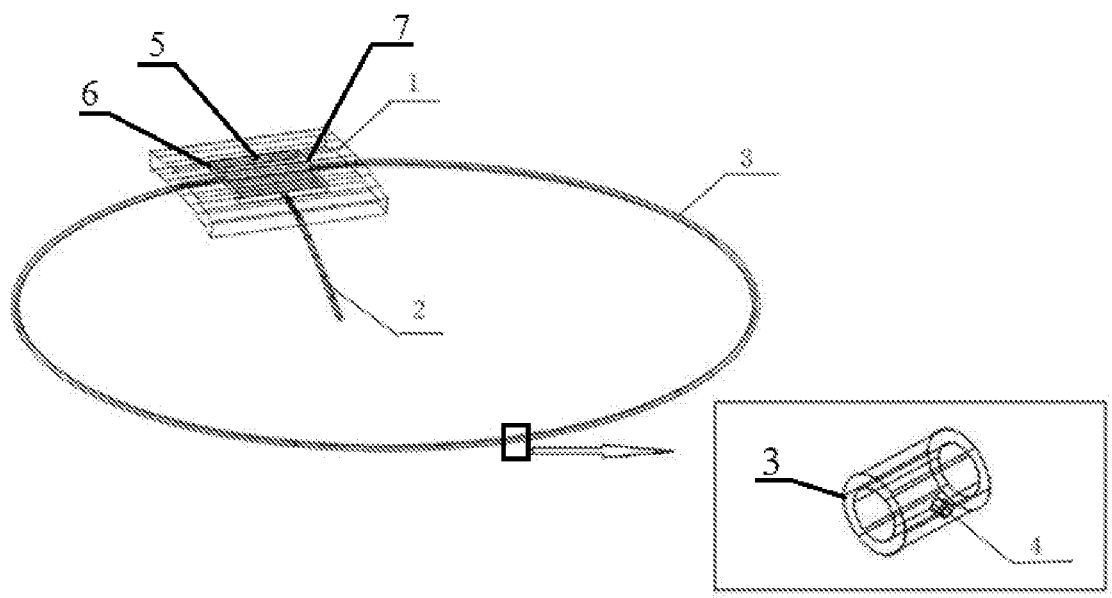
FIG. 1A is a schematic view showing the structure of the device of the present invention.
FIG. 1B is an enlarged view of a portion of an external catheter of the device of FIG. 1A.

The present invention will now be further described with reference to FIGS. 1A, 1B and 2. A glaucoma aqueous humor drainage device, in an embodiment, comprises a device body, wherein the device body comprises a pressure valve 1, the pressure valve 1 is connected with an internal drainage catheter 2 for draining anterior chamber aqueous humor from the anterior chamber into a cavity 5 within the pressure valve 1 and an external drainage catheter 3 for draining the anterior chamber aqueous humor in the cavity 5 of the pressure valve 1 to the ocular surface upon the pressure valve 1 reaching a threshold value. In an embodiment, the inner diameter of the internal drainage catheter is 1 mm, and the length of the internal drainage catheter is 8 mm.

The pressure valve is of a flat, and in some embodiments, a curved, structure, which fits the temporal sclera through the surface curvature, avoiding discomfort, and controls the opening and closing of the valve through the change of the pressure in the cavity.

In an embodiment, the pressure threshold of the pressure valve 1 is 12 mmHg. When the pressure of intraocular pressure exceeds the threshold pressure, such as 12 mmHg, the valve is opened, a drainage tube connected behind the valve drains aqueous humor to the ocular surface, relieving discomfort and dry eyes of the patient, and effectively draining off aqueous humor. The two ends of the external drainage catheter 3 are respectively connected to the left and right ends 6, 7 of the cavity 5 in the pressure valve 1 to form an annular closed structure. In an embodiment, the annular closed structure formed by the external drainage catheter 3 has a diameter of less than 30 mm.

Several through holes 4 are formed in the wall of the external drainage catheter 3, and anterior chamber aqueous humor is drained to the ocular surface of the eye through the through holes 4 in the wall of the external drainage catheter 3. The through holes 4 are sequentially distributed at 3, 6, 9 and 12 o'clock positions of the annular closed structure formed by the external drainage catheter 3 in a clock hands mode. The through hole 4 is a circular pore channel with a pore diameter of 500 μm.

The inner tube wall of the external drainage catheter 3 is also covered with a semi-permeable membrane material or the tube wall of the external drainage catheter 3 is made of the semi-permeable membrane material. In an embodiment, the semi-permeable membrane material has an ultrafiltration molecular weight of 500-500000 D and a pore size of 1 nm-1 μm.

Both the internal drainage catheter 2 and the external drainage catheter 3 are made of biocompatible materials.

One or more lead wires for fixing the external drainage catheter 3 through tension is further arranged on the external drainage catheter 3.

Figure 2:
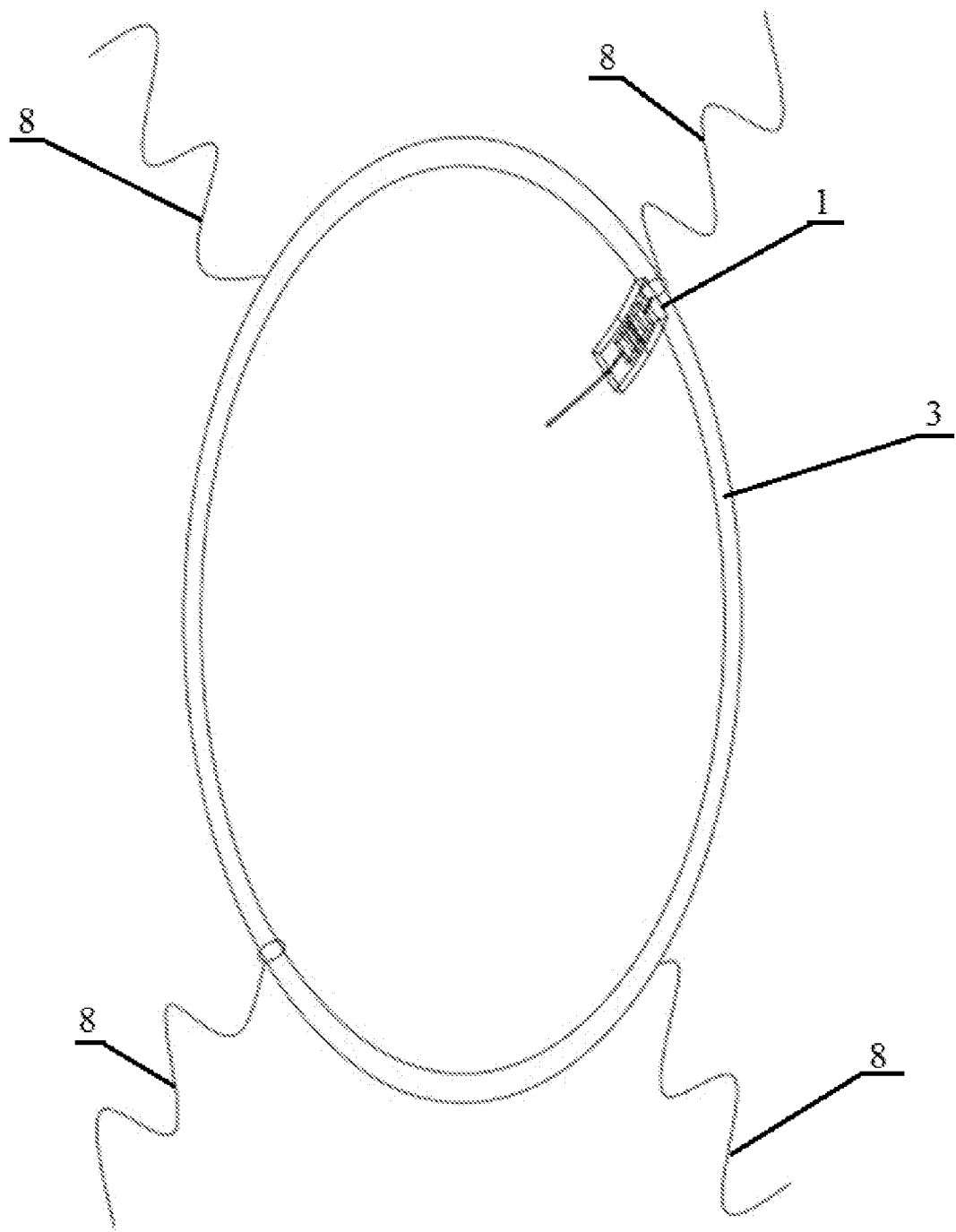
FIG. 2 is a schematic view showing another structure of the device of the present invention.

Another structure of the glaucoma aqueous humor drainage device of the present invention is shown in FIG. 2, wherein the wall of the external drainage catheter 3 is made of the semi-permeable membrane material. Since the production rate of normal human aqueous humor is 2.88-4.32 ml/day, the flow rate of the annular internal drainage catheter 2 made of the semi-permeable membrane material for the aqueous humor ocular surface drainage device is 3.6 ml/d, and the required filtration area is 80 $\mu m^2$. No additional tubular structure is required. The semi-permeable membrane material has an ultrafiltration molecular weight of 500-500000 D and a pore size of 1 nm-1 μm.

A glaucoma aqueous humor drainage method comprises the following steps: placing a patient in a supine position, carrying out surface anesthesia, and conventional disinfection and drape, after opening the eyelid of the surgery eye, flushing the conjunctival sac with diluted iodophor solution, moving an internal drainage catheter of a drainage device submerged under the superficial scleral flap 3-4 mm away from the corneal limbus, after reaching the corneal limbus, turning the internal drainage catheter into an included angle of 5°-10° with the iris to penetrate into the anterior chamber, after the internal drainage catheter is penetrated into the anterior chamber, fixing the internal drainage catheter on the surface of the superficial sclera by 8-0 absorbable line, placing a pressure valve along the radian of the sclera, opening the eyelid, and placing an external drainage catheter along the radian of the sclera and fixing under the fornix conjunctiva, and applying tobramycin dexamethasone eye ointment to the surgery eye after the surgery is finished. The external drainage catheter is located between the fornix conjunctiva and the corneal limbus and the distances away from the upper and lower parts of the fornix conjunctiva and the corneal limbus are all 8-10 mm.

In the description of the present invention, it should be noted the azimuth or positional relationship indicated by terms "center", "longitudinal", "horizontal", "upper", "lower", "front", "rear", "left", "right", "vertical", "horizontal", "top", "bottom", "inner", "outer", etc. is based on the azimuth or positional relationship shown in the drawings, only for the convenience of describing the present invention and simplifying the description, does not indicate or imply that the device or element referred to must have a specific orientation, be constructed and operated in a specific orientation, and therefore cannot be construed as limiting the present invention. Furthermore, the terms "first" and "second" are used for descriptive purposes only and are not to be construed as indicating or implying relative importance.

In describing the present invention, it is to be understood that, unless otherwise clearly specified and defined the terms "install", "connect", and "link" should be understood in a broad sense, for example, it can be a fixed connection, a detachable connection, or an integral connection; it can be a mechanical connection, it can also be an electrical connection; it can be directly connected, or it can be indirectly connected through an intermediary, or it can be a connection between two components. It will be understood by those of ordinary skill in the art that the specific meanings of the above terms in the present invention may be specifically understood. Further, in the description of the present invention, unless otherwise specified, "a plurality" means two or more.

One skilled in the art will recognize that: although the present invention has been described in accordance with the above specific embodiments, the inventive concept of the present invention is not limited to this invention, and any modifications using the inventive concept are intended to be included within the scope of this patent.

The above-mentioned embodiments are merely preferred embodiments of the present invention, and the scope of the present invention is not limited to the above-mentioned embodiments, and all technical solutions falling within the spirit of the present invention fall within the scope of the present invention. It should be noted that those skilled in the art will appreciate that various modifications and adaptations can be made without departing from the spirit and scope of the present invention.

What is claimed is:

1. A glaucoma-treatment method for draining aqueous humor using a glaucoma aqueous humor drainage device that includes an internal drainage catheter for draining the aqueous humor, a pressure valve connected to the internal drainage catheter, and an external drainage catheter connected to the pressure valve, the method comprising the following steps: moving the internal drainage catheter of the drainage device to be submerged under a superficial scleral flap of an eye 3-4 mm away from a corneal limbus of the eye, and after reaching the corneal limbus, turning the internal drainage catheter into an included angle of 5°-10° with an iris to penetrate into an anterior chamber of the eye, and after the internal drainage catheter is penetrated into the anterior chamber, fixing the internal drainage catheter on a surface of a superficial sclera of the eye using an absorbable line, placing the pressure valve along a radian of the sclera of the eye, opening an eyelid of the eye, and placing the external drainage catheter along the radian of the sclera and fixing under a fornix conjunctiva of the eye.

2. The method according to claim 1, wherein placing the pressure valve along the radian of the sclera comprises placing a pressure valve having a pressure threshold of 12 mmHg along the radian of the sclera.

3. The method according to claim 1, further comprising respectively connecting two ends of the external drainage catheter to a cavity in the pressure valve to form an annular closed structure.

4. The method according to claim 3, wherein a wall of the external drainage catheter is provided with several through holes, and the method further comprises draining anterior chamber aqueous humor to the ocular surface through the through holes in the wall of the external drainage catheter.

5. The method according to claim 3, wherein a wall of the external drainage catheter is made of a semipermeable membrane material.

6. The method according to claim 4, further comprising covering an inner wall of the external drainage catheter with a semipermeable membrane material.

7. The method according to claim 4, wherein the through-holes are sequentially distributed at 3, 6, 9 and 12 o'clock positions of the annular closed structure formed by the external drainage catheter in a clock-hands mode.

8. The method according to claim 4, wherein the through holes have circular pore channels with a pore size of 500 μm.

9. The method according to claim 1, wherein the internal drainage catheter has an inner diameter of 1 mm and a length of 8 mm.

10. The method according to claim 3, wherein a diameter of the annular closed structure formed by the external drainage catheter is less than 30 mm.

11. The method according to claim 1, wherein both the internal drainage catheter and the external drainage catheter are made of biocompatible materials.

12. The method according to claim 5, wherein the semipermeable membrane material has an ultrafiltration molecular weight of 500-500000 D and a pore size of 1 nm-1 μm.

13. The method according to claim 6, wherein the semipermeable membrane material has an ultrafiltration molecular weight of 500-500000 D and a pore size of 1 nm-1 μm.

14. A method according to claim 1, wherein the external drainage catheter is further provided with a lead for fixing the external drainage catheter through tension.

15. The method of claim 1, wherein the external drainage catheter is positioned between the fornix conjunctiva and the corneal limbus and distances away from upper and lower parts of the fornix conjunctiva and the corneal limbus are all 8-10 mm.

* * * * *